United States Patent
Kottenhahn et al.

[11] Patent Number: 5,907,044
[45] Date of Patent: May 25, 1999

[54] METHOD OF ISOLATING 1-[$N^2$-((S)-ETHOXYCARBONYL)-3-PHENYLPROPYL)-$N^6$-TRIFLUOROACETYL]-L-LYSYL-L-PROLINE (LISINOPRIL (TFA) ETHYL ESTER, LPE)

[75] Inventors: Matthias Kottenhahn, Freigericht; Roland Möller, Hammersbach; Michael Kraft, Rodenbach; Karlheinz Drauz, Freigericht; Klaus Stingl, Alzenau, all of Germany

[73] Assignee: Degussa Aktiengellschaft, Frankfurt, Germany

[21] Appl. No.: 08/951,579

[22] Filed: Oct. 16, 1997

[30] Foreign Application Priority Data

Jul. 30, 1997 [DE] Germany .............. 197 32 839

[51] Int. Cl.⁶ ............... C07D 207/20; C07D 207/12
[52] U.S. Cl. ............ 548/564; 548/533; 548/535
[58] Field of Search ............... 548/564, 533, 548/535

[56] References Cited

U.S. PATENT DOCUMENTS

| | | | |
|---|---|---|---|
| 4,172,077 | 10/1979 | Jovanovics et al. | 260/244.4 |
| 4,360,669 | 11/1982 | Schmidt et al. | 260/207.5 |
| 5,133,981 | 7/1992 | Harkrader et al. | 424/195.1 |
| 5,166,361 | 11/1992 | Zepp | 548/533 |
| 5,519,146 | 5/1996 | Ueda et al. | 548/533 |
| 5,616,727 | 4/1997 | Kottenhahn et al. | 548/533 |

FOREIGN PATENT DOCUMENTS 43 31 540 A1  9/1993  Germany .

*Primary Examiner*—Johann Richter
*Assistant Examiner*—Ebenezer Sackey
*Attorney, Agent, or Firm*—Pillsbury Madison & Sutro LLP

[57] ABSTRACT

A method of isolating 1-[$N^2$-((S)-ethoxycarbonyl)-3-phenylpropyl)-$N^6$-trifluoroacetyl]-L-lysyl-L-proline (lisinopril (TFA) ethyl ester, LPE). The solvent or solvent mixture used for the extraction is also a main constituent of the solvent or solvent mixture from which the crystallization takes place. High yield as well as good purity of the end product are obtained, without distillation. 1-[$N^2$-((S)-ethoxycarbonyl)-3-phenylpropyl)-$N^6$-trifluoroacetyl]-L-lysyl-L-proline (lisinopril (TFA) ethyl ester, LPE) is described as a precursor for producing an ACE inhibitor.

19 Claims, 2 Drawing Sheets

METHOD OF ISOLATING 1-[N²-((S)-ETHOXYCARBONYL)-3-PHENYLPROPYL)-N⁶-TRIFLUOROACETYL]-L-LYSYL-L-PROLINE (LISINOPRIL (TFA) ETHYL ESTER, LPE)

CROSS REFERENCE TO RELATED APPLICATION

This application claims priority from German Application No. 19732839.3, filed on Jul. 30, 1997, the subject matter of which is hereby incorporated herein by reference.

FIELD OF THE INVENTION

The invention relates to a method of isolating 1-[$N^2$-((S)-ethoxycarbonyl) -3-phenylpropyl) -$N^6$-trifluoroacetyl]-L-lysyl-L-proline (LPE, compound I).

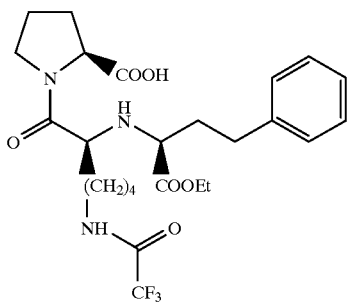

(I)

BACKGROUND OF THE INVENTION

N-substituted amino acids of this type are valuable intermediate products for the production of inhibitors of angiotensin-converting enzyme (ACE), which act as regulators of blood pressure. The compound of formula (I) is the direct intermediate product for 1-[$N^2$- ((S) -carboxy) -3-phenylpropyl)]-L-lysyl-L-proline (Lisinopril II), which exhibits superb therapeutic results in combating high blood pressure (Zestril®, Coric®, Prinivil®).

Compound (I) is obtained according to the state of the art by the reductive amination of 2-oxo-4-phenyl-ethyl butyrate with the dipeptide Lys (Tfa)-Pro.

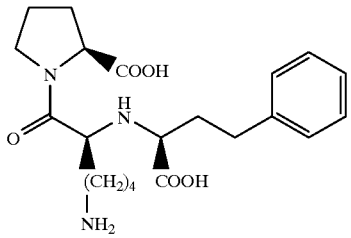

(II)

Such a method is described in the J. Org. Chem. 1988, 53, pp. 836–844. According thereto, compound (I) is obtained in a yield of 42% by basic extraction of the raw reaction solution, a subsequent extraction of the product in methylene chloride at pH 4.6 and, after a change of solvent, crystallization from methyl-tert.-butyl ether, cyclohexane.

EP 05 23 449 concerns the synthesis of compound (I) obtained according to example 3 with a yield of 60%. The workup of the raw reaction solution obtained according to this method contains, in addition to the basic and an acidic extraction step with 1,1,1-trichloroethane, a crystallization from methyl-tert. butyl ether.

In principle, other methods for producing compound (I) are also known which are not based on reductive amination but are less advantageous (EP 0 336 368 A2). The aqueous product phase is extracted therein with methylene chloride. However, after drying of the organic phase over sodium sulfate the solvent is again changed for crystallization in methyl-tert.-butyl ether.

The crystallization from pure methyl-tert.-butyl ether results in a crystal grain which is difficult to filter and in yields which are frequently insufficient (EP 0 645 398 A1). If compound (I) is allowed to crystallize out of solutions with a high concentration an additional recrystallization becomes necessary. The addition of cyclohexane (J. Org. Chem., 1988, 53, pp. 836–844) during the crystallization for increasing the yield is also described. However, there is the danger of a separation as oil, which makes it much more difficult to isolate the product, not only on an industrial scale.

EP 0 645 398 A1 extensively examines the possibility of the crystallization of compound (I) from various solvents or solvent mixtures. It is shown therein that when methyl-tert.-butyl ether or mixtures containing methyl-tert.-butyl ether are used the residual solvent content of the crystals is very great after the crystallization and residual solvent is bound in the crystal. The LPE raw material obtained in this manner is extremely difficult to dry. Long drying times which can adversely affect the product quality (formation of DKP, especially at elevated temperatures) and the tendency of the product to agglutinate makes special, expensive drying procedures necessary WO 95/07928 teaches a type of workup which describes an extraction with subsequent crystallization. The raw material of the LPE production is pre-cleaned in a pH range of 0–6.3, if necessary by means of several liquid/liquid extraction steps before it is crystallized out of a mixture of methyl-tert.-butyl ether and methyl cyclohexane at reduced temperatures. A solvent exchange also takes place between the extraction and the crystallization.

A disadvantage of the methods of the state of the art for working up LPE is the fact that frequently environmentally hazardous chlorinated solvents are used and the solvent must be replaced during the workup. This is difficult to achieve completely on an industrial scale and as a result of which only insufficiently defined solvent compounds can be adjusted for the crystallization. In addition, only mild temperature conditions are permitted for such solvent changes on account of the sensitivity of the product, which entails long distillation times. Moreover, the methods of the state of the art often result in crystals which are difficult to filter and much residual solvent is included therewith. Such a product requires long drying procedures which make it difficult to control caking and agglutination on an industrial scale.

SUMMARY OF THE INVENTION

In view of the state of the art indicated and discussed herein, the invention therefore has the purpose of finding a novel method for isolating LPE (I) which permits the raw material obtained from an LPE production process to be better isolated from an aqueous product phase with a simplified and more economic process, which for its part helps reduce the customary long drying times which stress the LPE (I) and more favorable crystalline properties of the precipitated material are obtained.

The invention also has the purpose of generating an end LPE material using the novel, simpler isolating methods which end material is improved over that of the state of the art with comparable drying times, especially as concerns the residual solvent content.

The invention also has the purpose of providing an improved LPE (I).

As a result of the fact that LPE (I) is extracted with a solvent or solvent mixture from an aqueous product solution of an LPE production process produced according to the method of the state of the art and that this solvent or solvent mixture is subsequently used as a main component of the solvent or solvent mixture from which the LPE (I) is crystallized, crystals of LPE distinguished by more advantageous crystalline properties are obtained by this simplified and much more economic method. The LPE generated in this manner exhibits only slight solvent inclusion after crystallization and possesses excellent filterability on account of its well-formed crystalline structure. The slight amount of included residual solvent is a reason that the previous long drying times per drying batch can be significantly reduced. The LPE produced in this manner has a byproduct content which is just as excellently low as that of the state of the art. Thus, a product which is more advantageous in comparison to the state of the art can surprisingly be produced in spite of the simplified method of extraction and crystallization of LPE, which is a reason that a more cost-effective method for the production of LPE can be made available.

DETAILED DESCRIPTION OF THE INVENTION

Figure 1:
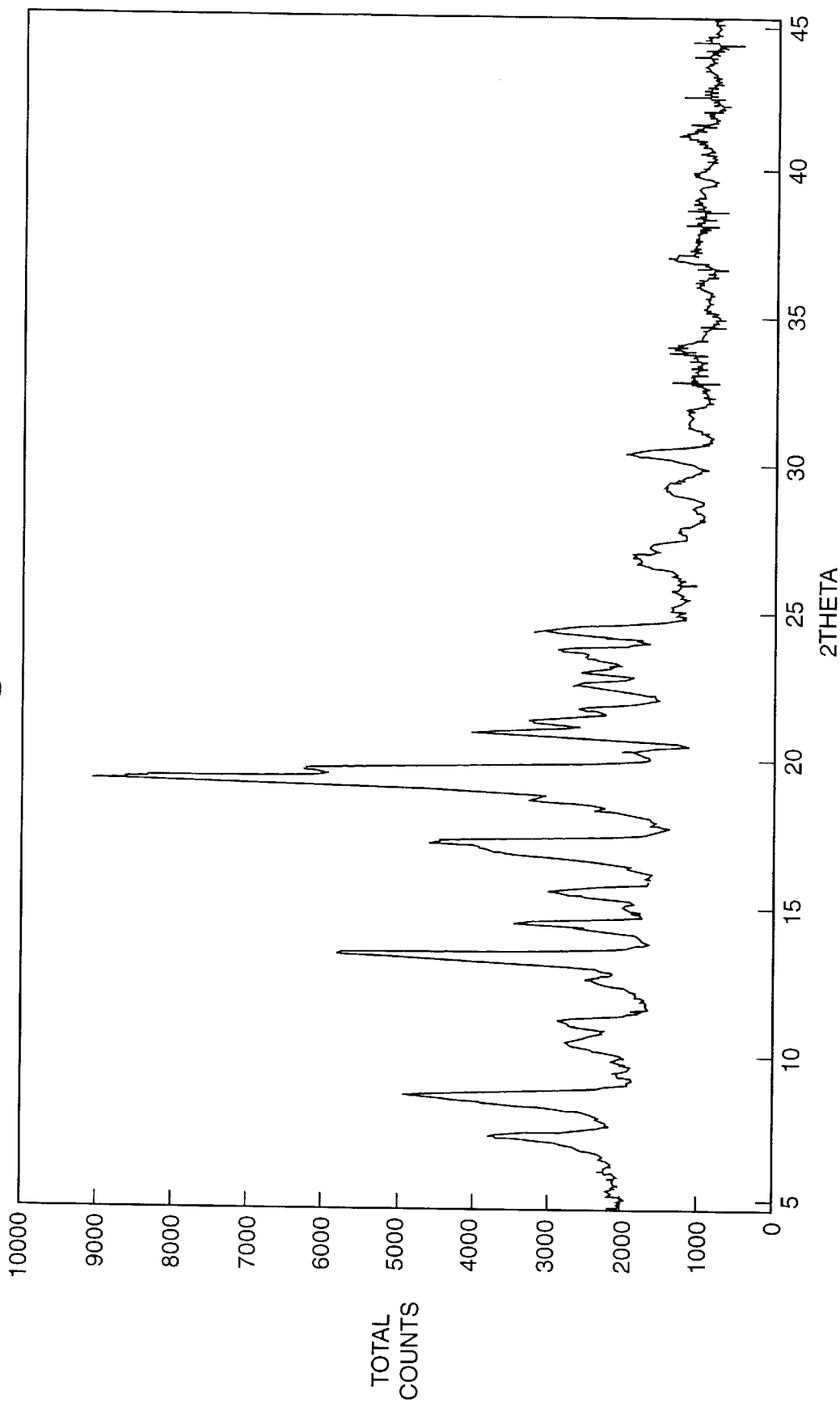
FIG. 1 shows, graphically, x-ray diffraction reflexes of LPE (I) of the prior art.

It is especially advantageous if the novel method for the extraction and crystallization of LPE (I) is carried out with solvents or solvent mixtures consisting of esters and/or ketones of the general formula (III)

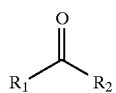
(III)

which solvents or solvent mixtures can be additionally mixed, if necessary, with open-chain aliphatic or cycloaliphatic hydrocarbons as solvent.

The groups $R_1$ and $R_2$ therein advantageously stand-for a group of $(C_1-C_6)$ alkyl groups. These groups can be linear or branched. In particular, the groups can contain: methyl, ethyl, n-propyl, isopropyl, n-butyl, sec-butyl, isobutyl, tert.-butyl, n-pentyl, n-hexyl. Group $R_2$ comprises the group of group $R_1$ and also the group of the $(C_1-C_6)$ alkoxy groups. The latter can also be linear or branched. The following are, in particular, suitable for $R_2$: methoxy, ethoxy, n-propoxy, isopropoxy, n-butoxy, sec-butoxy, isobutoxy, tert.-butoxy, n-pentoxy, n-hexoxy. The mixing of the solvent or solvent mixture with the hydrocarbons can be carried out before or even after the extraction. These hydrocarbons are open-chain aliphatic hydrocarbons which contain 5–9 C atoms. They can be linear or branched as desired. "Cycloaliphatic hydrocarbons" denotes rings having 5 to 7 C atoms which can be substituted as desired with $(C_1-C_4)$ alkyl groups which can be present in branched form. The following have proven to be quite especially advantageous solvents and solvent mixtures:

Esters—Ethyl acetate, n-propyl acetate, n-butyl acetate, ethyl propionate

Ketones—Methyl isobutyl ketone, diethyl ketone, methyl isopropyl ketone

Aliphatics—n-pentane, n-hexane, cyclohexane, methyl cyclohexane.

Higher homologs of the solvents described above are also suitable, with a natural boundary resulting on account of the rising boiling points and therewith a deterioration of the drying properties of the moist crystallizate. Any combination of the above-named, especially advantageous solvents have proven to be especially advantageous solvent mixtures.

These solvents and/or solvent mixtures can also be used with advantage for pre-cleaning the aqueous product phase at a pH between 0 and 3.5. This pre-cleaning takes place before the actual extraction of the LPE (I) in the organic phase, and has the result that the aqueous product phase includes few byproducts. Since the same solvents and/or solvent mixtures can be used which can also be used for the extraction and crystallization, the necessity of making available additional storage capacity for solvents and/or solvent mixtures which differ from those of the extraction and crystallization of the LPE (I) is advantageously reduced. Likewise, this clearly improves the possibility of recycling the solvents. It is consequently always especially advantageous in an industrial process to use as few different solvents as possible.

In addition, an advantageous embodiment of the method can be seen in that an activated carbon purification can be carried out in the same pH range of 0–3.5 after the solvent treatment described above but before the actual extraction of the LPE (I) into an organic solvent or solvent mixture. This again clearly improves the ability of the LPE (I) to be crystallized.

The extraction of the LPE (I) described above from its aqueous product phase is subsequently carried out in a pH range between 3.5 and 6.3, especially preferably 3.9 to 4.8. It is quite especially preferred that the organic solution of LPE (I) obtained in this manner is washed before the crystallization with water at a pH of 4.8 to 6.3 —a range of 5.7 to 6.0 is especially preferred—and that the aqueous phase is separated from the organic phase.

According to the invention the LPE extraction solution can be azeotropically dehydrated before the concluding crystallization, if necessary by distillation. The indicated solvents and solvent mixtures function thereby as water-entraining medium.

The extraction steps discussed above are advantageously carried out at a temperature between 0° C. and 60° C., preferably at 20° C. to 50° C. and especially preferably at 35° C. to 45° C. If solvent mixtures are used volumetric ratios between esters and/or ketones and the aliphatic/cycloaliphatic hydrocarbons used of between 1:0.01 and 1:100, quite especially advantageously 1:0.5 to 1:2 are used. The concluding crystallization takes place according to the invention at temperatures between −40° C. and +50° C. After the crystallization an aliphatic or cycloaliphatic hydrocarbon like that already described in detail above can be added with advantage once more, optionally after the mother liquor has been evaporated to low bulk, to the latter. This results in a new crystallization during which the yields of >75% of LPE (I) which were already high in the past can be increased again by approximately 10%.

The present invention also comprises a novel LPE (I) distinguished by a novel and advantageous crystal modification. LPE (I) produced according to the prior state of the art exhibits a completely different X-ray diffraction behavior than one obtained according to the present invention. Significant new, different reflexes in an X-ray diffraction of the novel LPE (I) in a transmission diffractometer manufactured by STOE/Darmstadt are shown in Table 1.

TABLE 1

| No. | 2 Theta |
|-----|---------|
| 1 | 6.7241 |
| 2 | 9.4851 |
| 3 | 11.9034 |
| 4 | 16.3074 |
| 5 | 17.8722 |

Diffractometer: Transmission
Monochromator: Curved Ge (111)
Wavelength: 1.540598 Cu
Detector: Curved PSD
Scan mode: Transmission/stationary PSD/fixed omega 2Theta scan The reflexes shown in Table 1 have a relative intensity of $\geq$ 30% of the main reflex at 21.2663. The tolerance of the 2Theta values is maximally ±10%. A deviation of ±5% is preferred and the uncertainty is quite especially preferred at ±1%. However, errors of not greater than ±0.02 units usually occur in apparatus which has been properly adjusted and calibrated.

Figure 2:
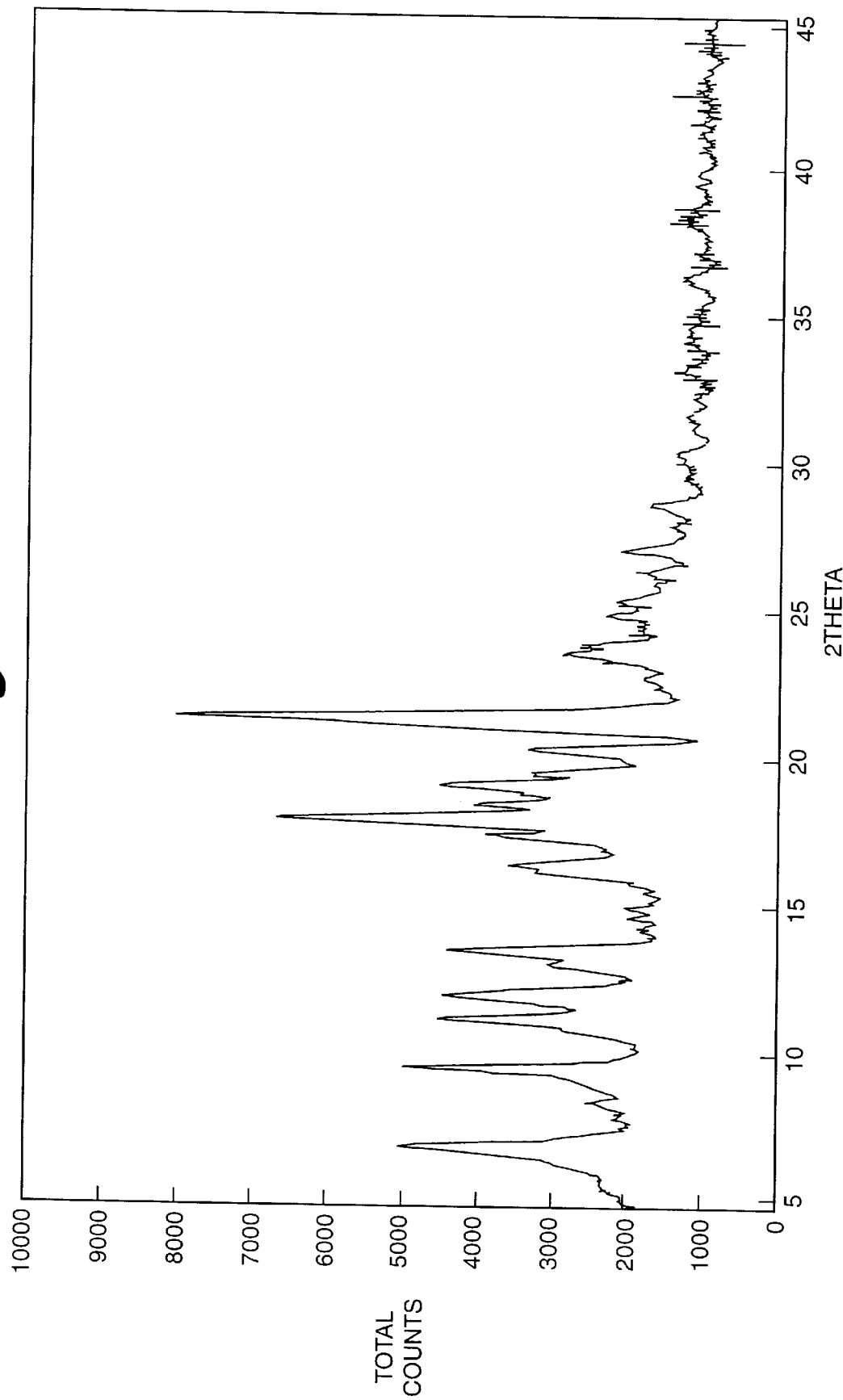
FIG. 2 shows, graphically, x-ray diffraction reflexes of LPE (I) of the subject invention.

FIGS. 1 and 2 contrast the X-ray diagrams of two LPE specimens. FIG. 1 shows the reflexes of an LPE (I) produced according to the state of the art (method according to EP 0 719 279, comparative Example 1, completely dried product). FIG. 2 shows results from a specimen obtained according to Example 8 of the present invention. However, all X-ray diagrams of the specimens of examples 2–10 show equal reflex distributions and equal relative intensities.

This novel crystal modification has the result that the LPE (I) can be filtered especially well.

According to the invention the drying times of the LPE (I) produced in this manner are significantly below those of the state of the art. The finding of the novel crystal modification was therewith causal for the possibility of being able to carry out the LPE production method in an economically more advantageous manner.

The following non-limiting examples are intended to clarify the invention.

COMPARATIVE EXAMPLE 1

1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated for 10 min. and the phases subsequently separated. A pH of 4 was now adjusted at 5° C. in the aqueous phase and the latter extracted with 400 ml ethyl acetate. The phases were separated, the organic phase mixed with 110 ml water and adjusted with sodium hydroxide solution (50%) to a pH of 5.8. After phase separation the organic phase was largely evaporated to low bulk in a vacuum at max. 33° C. bottom temperature. The bottom was mixed with 125 ml toluene and evaporated further to low bulk to 120 g. Thereafter, 240 ml methyl-tert.-butyl ether were added and cooled down to +4° C. A crystalline precipitate was produced thereby. To this crystalline suspension, 50 ml methyl cyclohexane were added dropwise at 4° C. within 3 h. The mixture was then agitated 1 h, filtered, washed and subsequently dried in an oil pump vacuum 4 h at RT.

Yield: 67.7 g (85.2% of theoretical)

Analytics:

| SSS diastereomer content (% by weight) | Melting point (° C.) | Residual solvent (mg/kg) | $(\alpha)25$/D (c = 1 MeOH/ 0.IN HCl) (degrees) |
|---|---|---|---|
| 92.0(+−0.4) | n.d. | 6400 toluene 49100 methyl-tert.- dibutyl ether 770 methyl cylcohexane | −24.0 |

(n.d. = not determined)

EXAMPLE 2

1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated for 10 min. and the phases subsequently separated. A pH of 4 was now adjusted at 40° C. in the aqueous phase and the latter extracted with 450 ml ethyl acetate. The phases were separated, the organic phase mixed with 110 ml water and adjusted with sodium hydroxide solution (50%) to a pH of 5.8. After phase separation 235 ml methyl cyclohexane were added to the organic phase and evaporated to low bulk in a vacuum at max. 40° C. bottom temperature to 290 g. The bottom was cooled down to −5° C. A crystalline precipitate was produced which was filtered, washed and subsequently dried in an oil pump vacuum 4 h at RT.

Yield: 48.0 g (60.5% of theoretical)

Analytics:

| SSS diastereomer content (% by weight) | Melting point (° C.) | Residual solvent (mg/kg) | $(\alpha)25$/D (c = 1 MeOH/ 0.IN HCl) (degrees) |
|---|---|---|---|
| 98.3(+−0.3) | 85–90 | n.n. ethyl acetate 126 methyl cyclohexane | −25.2 |

(n.n. = cannot be demonstrated)

EXAMPLE 3
1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.
Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated for 10 min. and the phases subsequently separated. A pH of 4 was now adjusted at 40° C. in the aqueous phase and the latter extracted with 450 ml ethyl propionate. The phases were separated, the organic phase mixed with 110 ml water and adjusted with sodium hydroxide solution (50%) to a pH of 5.8. After phase separation 225 ml methyl cyclohexane were added to the organic phase and evaporated to low bulk in a vacuum at max. 40° C. bottom temperature to 270 g. The bottom was mixed with 250 ml methyl cyclohexane and cooled down to +5° C. A crystalline precipitate was produced which was filtered, washed and subsequently dried in an oil pump vacuum 4 h at RT.

Yield: 59.9 g (75.4% of theoretical)
Analytics:

| SSS diastereomer content (% by weight) | Melting point (° C.) | Residual solvent (mg/kg) | $(\alpha)25/D$ (c = 1 MeOH/ 0.1N HCl) (degrees) |
|---|---|---|---|
| 96.8(+−0.8) | 87–90 | <20 ethyl propionate- 598 methyl cyclohexane | −25.5 |

EXAMPLE 4
1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.
Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated 10 min and the phases subsequently separated. A pH of 4 was now adjusted at 40° C. in the aqueous phase and the latter extracted with 450 ml n-propyl acetate. The phases were separated, the organic phase mixed with 110 ml water and adjusted with sodium hydroxide solution (50%) to a pH of 5.8. After phase separation 300 ml n-hexane were added to the organic phase and evaporated to low bulk in a vacuum at max. 40° C. bottom temperature to 240 g. The bottom was mixed with 206 ml n-hexane and cooled down to +5° C. A crystalline precipitate was produced which was filtered, washed and subsequently dried in an oil pump vacuum 4 h at RT.

Yield: 54.8 g (69% of theoretical)
Analytics:

| SSS diastereomer content (% by weight) | Melting point (° C.) | Residual solvent (mg/kg) | $(\alpha)25/D$ (c = 1 MeOH/ 0.1N HCl) (degrees) |
|---|---|---|---|
| 97.0(+−0.6) | 87–91 | <20 n-propyl acetate 43 n-hexane | −25.4 |

EXAMPLE 5
1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.
Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml ethyl propionate. The phases were separated, the organic phase mixed with 110 ml water and adjusted with sodium hydroxide solution (50%) to a pH of 5.8. After phase separation the organic phase was evaporated to low bulk in a vacuum at max. 40° C. bottom temperature to 230 g. The bottom was mixed with 275 ml cyclohexane and cooled down to +50° C. A crystalline precipitate was produced which was filtered, washed and subsequently dried in an oil pump vacuum 4 h at RT.

Yield: 60.0 g (75.6% of theoretical)
Analytics:

| SSS diastereomer content (% by weight) | Melting point (°C.) | Residual solvent (mg/kg) | $(\alpha) 25/D$ (c = 1 MeOH/ 0.1N HCl) (degrees) |
|---|---|---|---|
| 97.4 (+−0.8) | 87–91 | <20 ethyl propionate 524 cyclohexane | −25.3 |

EXAMPLE 6
1-[$N^2$-((S)-ethoxycarbonyl)-3-phenylpropyl]-$N^6$-trifluoroacetyl]-L-lysyl-L-proline (compound I)

A reductive amination according to patent application EP 05 23 449 is carried out analogously to Example 3, page 10.
Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml n-propyl acetate. The phases were separated, the organic phase mixed with 110 ml water and adjusted with sodium hydroxide solution (50%) to a pH-of 5.8. After phase separation the organic phase was evaporated to low bulk in a vacuum at max. 40° C. bottom temperature to 200 g. The bottom was mixed with 270 ml cyclohexane and cooled down to +5° C. A crystalline precipitate was produced which was filtered, washed and subsequently dried in an oil pump vacuum 4 h at RT.

Yield: 56.5 g (71.2% of theoretical)

Analytics:

| SSS diastereomer content (% by weight) | Melting point (°C.) | Residual solvent (mg/kg) | ($\alpha$) 25/D (c = 1 MeOH/ 0.1N HCl) (degrees) |
|---|---|---|---|
| 97.6 (+−0.2) | 87–91 | <20 propyl acetate 253 cyclohexane | −25.4 |

EXAMPLE 7

1-[$N^2$-((S)-ethoxycarbonyl)-3-phenylpropyl)-$N^6$-trifluoroacetyl]-L-lysyl-L-proline (compound I)

A reductive amination according to patent application EP 05 23 449 is carried out analogously to Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml methyl isobutyl ketone. The phases were separated, the organic phase mixed with 110 ml water and adjusted with sodium hydroxide solution (50%) to a pH of 5.8. After phase separation the organic phase was evaporated to low bulk in a vacuum at max. 40° C. bottom temperature to 230 g. The bottom was mixed with 185 ml methyl cyclohexane and cooled down to +5° C. A crystalline precipitate was produced which was filtered, washed and subsequently dried in an oil pump vacuum 4 h at RT.

Yield: 56.1 g (70.6% of theoretical)

Analytics:

| SSS diastereomer content (% by weight) | Melting point (°C.) | Residual solvent (mg/kg) | ($\alpha$) 25/D (c = 1 MeOH/ 0.1N HCl) (degrees) |
|---|---|---|---|
| 97.6 (+−0.6) | 87–91 | 91 methyl isobutyl ketone 253 methyl cyclohexane | −25.5 |

EXAMPLE 8

1-[$N^2$-((S)-ethoxycarbonyl)-3-phenylpropyl)-$N^6$-trifluoroacetyl]-L-lysyl-L-proline (compound I)

A reductive amination according to patent application EP 05 23 449 is carried out analogously to Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 120 ml toluene and 30 ml ethyl acetate the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml methyl isobutyl ketone. The phases were separated, the organic phase mixed with 110 ml water and adjusted with sodium hydroxide solution (50%) to a pH of 5.8. After phase separation the organic phase was evaporated to low bulk in a vacuum at max. 40° C. bottom temperature to 185 g. The bottom was mixed with 235 ml cyclohexane and cooled down to +5° C. A crystalline precipitate was produced which was filtered, washed and subsequently dried in an oil pump vacuum 4 h at RT.

Yield: 60.5 g (76.2% of theoretical)

Analytics:

| SSS diastereomer content (% by weight) | Melting point (°C.) | Residual solvent (mg/kg) | ($\alpha$) 25/D (c = 1 MeOH/ 0.1N HCl) (degrees) |
|---|---|---|---|
| 98.4 (+−0.5) | 87–91 | 207 methyl isobutyl ketone 226 cyclohexane | −25.4 |

EXAMPLE 9

1-[$N^2$-((S)-ethoxycarbonyl)-3-phenylpropyl)-$N^6$-trifluoroacetyl]-L-lysyl-L-proline (compound I)

A reductive amination according to patent application EP 05 23 449 is carried out analogously to Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 45 ml methyl isobutyl ketone and 45 ml cyclohexane the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml methyl isobutyl ketone. The phases were separated, the organic phase mixed with 110 ml water and adjusted with sodium hydroxide solution (50%) to a pH of 5.8. After phase separation the organic phase was evaporated to low bulk in a vacuum at max. 40° C. bottom temperature to 185 g. The bottom was mixed with 235 ml cyclohexane and cooled down to +5° C. A crystalline precipitate was produced which was filtered, washed and subsequently dried in an oil pump vacuum 4 h at RT.

Yield: 61 g (76.8% of theoretical)

Analytics:

| SSS diastereomer content (% by weight) | Melting point (°C.) | Residual solvent (mg/kg) | (α) 25/D (c = 1 MeOH/ 0.IN HCl) (degrees) |
|---|---|---|---|
| 98.6 (+−0.4) | 87–91 | 215 methyl isobutyl ketone 280 cyclohexane | −25.6 |

EXAMPLE 10

1-[$N^2$-((S)-ethoxycarbonyl)-3-phenylpropyl)-$N^6$-trifluoroacetyl]-L-lysyl-L-proline (compound I)

A reductive amination according to patent application EP 05 23 449 is carried out analogously in Example 3, page 10.

Workup:

The reaction solution, for which the dosage for the workup was selected in such a manner that in addition to the typical byproduct profile altogether 150 mmol of the desired LPE-(SSS)-diastereomer (I) were in it, was largely concentrated by evaporation in a vacuum at 45° C. bath temperature. The residue was taken up in 1400 ml water and briefly stripped in a vacuum. After the addition of 45 ml methyl isobutyl ketone and 45 ml cyclohexane the pH was adjusted with concentrated hydrochloric acid to 1. The mixture was then agitated 10 min. and the phases subsequently separated. A pH of 4 was now adjusted at 40° C. in the aqueous phase and the latter extracted with 450 ml methyl isobutyl ketone. The phases were separated, the organic phase mixed with 110 ml water and adjusted with sodium hydroxide solution (50%) to a pH of 5.8. After phase separation the organic phase was evaporated to low bulk in a vacuum at max. 40° C. bottom temperature to 160 g. The bottom was mixed with 175 ml cyclohexane and cooled down to +5° C. A crystalline precipitate was produced thereby. To this crystalline suspension, 103 ml. cyclohexane was added dropwise at 5° C. within 1.5 hr. The mixture was then agitated for 1 hr., filtered, washed and subsequently dried in an oil pump vacuum 4 h at RT.

Yield: 66.0 g (83.1% of theoretical)

Analytics:

| SSS diastereomer content (% by weight) | Melting point (°C.) | Residual solvent (mg/kg) | (α) 25/D (c = 1 MeOH/ 0.IN HCl) (degrees) |
|---|---|---|---|
| 97.4 (+−0.3) | 87–91 | 167 methyl isobutyl ketone 218 cyclohexane | −25.6 |

What is claimed is:

1. A method of isolating LPE of formula (I)

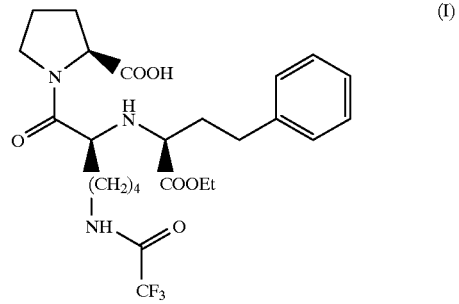

from an aqueous solution in an LPE production process by extraction and subsequent crystallization, comprising using a solvent or solvent mixture excluding methyl-tert. butyl ether to extract the LPE of formula (I) which solvent or solvent mixture is also a main constituent of a solvent or solvent mixture used for the crystallization.

2. The method according to claim 1, comprising using esters and/or ketones of the general formula (III) as the solvents or solvent mixtures

wherein $R_1=(C_1-C_6)$ alkyl, and
$R_2=(C_1-C_6)$ alkyl or $(C_1-C_6)$ alkoxy, optionally mixed with open-chain aliphatic or cycloaliphatic hydrocarbons as solvent, the hydrocarbons being added to the solvent or solvent mixture before or after the extraction.

3. The method according to claim 1, comprising, prior to the extraction, treating the aqueous product phase at a pH between 0 and 3.5 with the solvent or solvent mixtures and subsequently separating off an aqueous product phase.

4. The method according to claim 3, comprising carrying out an activated carbon purification in a pH range of 0 to 3.5 before the extraction of the LPE (I) into the organic phase and after the treatment of the aqueous product phase with one of the solvents or solvent mixtures.

5. The method according to claim 1, comprising carrying out the extraction of the LPE (I) from the aqueous solution at a pH between 3.9 and 4.8.

6. The method according to claim 1, comprising washing out the organic LPE extraction solution with water at a pH of 4.8 to 6.3, before the crystallization, and separating out the aqueous phase.

7. The method according to claim 1, comprising washing out the organic LPE extraction solution with water at a pH of 5.7 to 6.0, before the crystallization, and separating out the aqueous phase.

8. The method according to claim 1, comprising azeotropically dehydrating the LPE extraction solution by distillation before the crystallization.

9. The method according to claim 5, comprising carrying out the extraction at temperatures between 0° C. and 60° C.

10. The method according to claim 6, comprising carrying out the extraction at temperatures between 0° C. and 60° C.

11. The method according to claim 7, comprising carrying out the extraction at temperatures between 0° C. and 60° C.

12. The method according to claim 2, comprising using a volumetric ratio of the ester and/or ketone and the aliphatic/ cycloaliphatic hydrocarbon in the solvent mixture of between 1:0.01 and 1:100.

13. The method according to claim 1, wherein the temperature during crystallization is between −40° C. and +50° C.

14. The method according to claim 2, wherein the temperature during crystallization is between −40° C. and +50° C.

15. The method according to claim 9, further comprising, after the crystallization, adding an aliphatic or cycloaliphatic hydrocarbon to the mother liquor, after the mother liquor has been evaporated to low volume, to complete the crystallization.

16. The method according to claim 10, further comprising, after the crystallization, adding an aliphatic or cycloaliphatic hydrocarbon to the mother liquor, after the mother liquor has been evaporated to low volume, to complete the crystallization.

17. The method according to claim 11, further comprising, after the crystallization, adding an aliphatic or cycloaliphatic hydrocarbon to the mother liquor, after the mother liquor has been evaporated to low volume, to complete the crystallization.

18. The method according to claim 1, comprising a crystallization step which yields LPE of formula (I) with reflexes at 6.7241

9.4851

11.9034

16.3073

17.8722 (2 theta).

19. The method according to claim 1, wherein the solvent or solvent mixture used to extract the LPE of formula (I) consists essentially of at least one member selected from the group consisting of esters, ketones and open chain aliphatic or cycloaliphatic hydrocarbons.

* * * * *